(12) United States Patent
Fuchs

(10) Patent No.: US 9,116,115 B2
(45) Date of Patent: Aug. 25, 2015

(54) APPARATUS AND METHOD FOR DETERMINING THE HOMOGENEITY OF A FLUID FLOW

(75) Inventor: Christian Fuchs, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 725 days.

(21) Appl. No.: 13/440,250

(22) Filed: Apr. 5, 2012

(65) Prior Publication Data
US 2012/0256631 A1    Oct. 11, 2012

(30) Foreign Application Priority Data
Apr. 5, 2011    (DE) .......................... 10 2011 006 750

(51) Int. Cl.
| | |
|---|---|
| G01N 21/3504 | (2014.01) |
| G01V 8/00 | (2006.01) |
| G01N 24/08 | (2006.01) |

(52) U.S. Cl.
CPC .......... *G01N 21/3504* (2013.01); *G01N 24/082* (2013.01); *G01N 24/085* (2013.01); *G01V 8/00* (2013.01); *F01N 2610/02* (2013.01); *F01N 2610/148* (2013.01)

(58) Field of Classification Search
USPC ............... 324/300–322; 356/128, 237.1, 609; 210/93; 73/290 R; 60/276; 250/255
See application file for complete search history.

(56) References Cited

U.S. PATENT DOCUMENTS

| | | | | |
|---|---|---|---|---|
| 2,884,783 | A | * | 5/1959 | Spengler et al. ............ 73/290 R |
| 3,459,304 | A | * | 8/1969 | Brenchley ........................ 210/93 |
| 5,009,064 | A | * | 4/1991 | Grob et al. ....................... 60/276 |
| 5,694,210 | A | * | 12/1997 | Newell et al. .................. 356/128 |
| 5,729,013 | A | * | 3/1998 | Bergren, III .................... 250/255 |
| 6,081,324 | A | * | 6/2000 | Yagita et al. ................. 356/237.1 |
| 2007/0153296 | A1 | * | 7/2007 | Schick ........................... 356/609 |
| 2012/0256631 | A1 | * | 10/2012 | Fuchs ............................ 324/320 |

* cited by examiner

*Primary Examiner* — Dixomara Vargas
*Assistant Examiner* — Tiffany Fetzner
(74) *Attorney, Agent, or Firm* — Michael Best & Friedrich LLP

(57) ABSTRACT

An apparatus for determining the homogeneity of a fluid flow in a pipe, such as a reducing-agent flow in an exhaust-gas pipe of an internal combustion engine, including a transmitter arranged on a light-transmissive region of the pipe and a diametrically opposite detector. The transmitter and detector being coupled such that they are rotatable through an angle of 360° about a rotational axis which is located substantially in the axis of symmetry of the pipe. The transmitter and the detector are rotated through at least 360° about the rotational axis, thus capturing an intensity of the detected light over the rotation angle, and from this a homogeneity of the fluid flow is deduced.

14 Claims, 3 Drawing Sheets

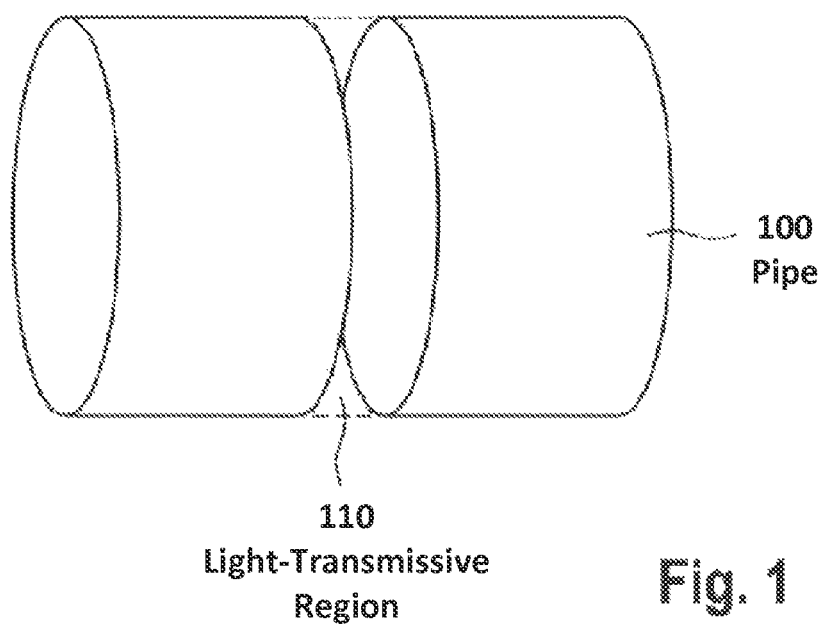

APPARATUS AND METHOD FOR DETERMINING THE HOMOGENEITY OF A FLUID FLOW

BACKGROUND OF THE INVENTION

The invention relates to an apparatus and to a method for determining the homogeneity of a fluid flow in a pipe.

In today's vehicles with internal combustion engines, various components for the aftertreatment of exhaust gases are provided in the exhaust strand. In the case of spark-ignition engines, these components are for example three-way catalytic converters. In diesel motors, particulate filters are usually provided nowadays to reduce the soot particulate emissions. Moreover, for example SCR catalytic converter systems or NSC systems are provided to reduce the nitrogen oxide emissions. In the SCR catalytic converter systems, an SCR (Selective Catalytic Reduction) catalytic converter is arranged in the exhaust gas region, which reduces the nitrogen oxides ($NO_x$) contained in the exhaust gas of the internal combustion engine to nitrogen ($N_2$) in the presence of a reducing agent. Such SCR catalytic converters are moreover used in exhaust gas systems of combustion plants, waste incineration plants, gas turbines and industrial plants.

Owing to SCR, the proportion of nitrogen oxides in the exhaust gas can be significantly reduced. For the activity of the reduction, ammonia ($NH_3$) is required, which is admixed to the exhaust gas and reacts with the nitrogen oxides to form nitrogen and water. The reducing agents used here are $NH_3$ or reagents which give off ammonia. In the motor vehicle sector, a 32.5% aqueous urea solution (urea-water solution; UWS) is typically used in accordance with DIN 70070, and is commercially available under the tradename AdBlue. This solution is injected into the exhaust strand upstream of the SCR catalytic converter by means of an injection system. In a hydrolysis catalytic converter arranged upstream of the SCR catalytic converter, $NH_3$, which acts as a reducing agent, is generated from said solution. For optimum operation of the entire system, it is advantageous if the reducing agent is introduced into the catalytic converter as uniformly as possible. Introduction which is as uniform as possible in this case means as homogeneous a distribution of the reducing agent in the reducing-agent flow as possible. For this reason it is of interest to examine the reducing-agent flow and to specify a measurement method for determining the distribution of the reducing agent upstream of the catalytic converter so as to permit assessment of the functionality of the entire system.

SUMMARY OF THE INVENTION

A method for determining the reducing-agent distribution practised on-site by the applicant is the targeted gas removal using a thin pipe at various locations of the flow. This method, however, is time-consuming and can, therefore, provide only information relating to mean values over time for variables characterizing the flow. The invention is based on the object of specifying an apparatus and a method, which can provide reliable information relating to the reducing-agent distribution in the exhaust-gas pipe of an internal combustion engine and in particular relating to the homogeneity of a reducing-agent flow in an exhaust-gas pipe of an internal combustion engine or generally to the homogeneity of a fluid flow in a pipe. In the present case, homogeneity refers to the uniform distribution of the reducing agent in the flow over a given diameter, in particular and ideally over the diameter of the pipe or exhaust-gas pipe.

In one embodiment, the apparatus according to the invention is characterized by at least one transmitter, which is arranged on a light-transmissive region of the pipe, and at least one diametrically opposite detector, with transmitter and detector being coupled such that together they are rotatable through an angle of 360° about a rotational axis which is substantially located in the axis of symmetry of the pipe. Beside a rotatable arrangement of transmitter and detector, it is also possible purely as a matter of principle to arrange a plurality of transmitters and detectors, which are assigned to one another, around the circumference of the pipe in each case at an angular offset, in particular at identical angular offsets, so as to simulate, as it were, the rotation. In this case, it is no longer necessary for the arrangement to be rotatable. However, it would have to be ensured in this case that the signal emitted by a transmitter, for example light, is detected only by the detector located opposite it, and that no signals stray into another, in particular neighbouring, detector. When this application mentions "rotatable" or "rotatability", this does not only refer to the physical rotatability of one transmitter and one detector, but it analogously also refers to a previously described arrangement of a plurality of transmitters and in each case diametrically opposite detectors, which are arranged in each case with an angular offset.

The invention also provides at least one method for determining the homogeneity of a fluid flow in a pipe, in particular of a reducing-agent flow in an exhaust-gas pipe of an internal combustion engine. The method, using for example, the apparatus described, makes provision for the transmitter and the detector to be rotated through at least 360° about the rotational axis which is located substantially in the longitudinal axis of the pipe and in the process capture the intensity of the detected light over this rotation angle and for the homogeneity of the fluid flow, in particular of the reducing-agent flow, to be gathered from this. The method and the apparatus take advantage of the Beer-Lambert law, which describes the attenuation of the radiation intensity of the path length when passing through an absorbing substance and has been known for a long time in modern photometry as an analytical method. The invention is based on the idea of reaching a conclusion about the homogeneity of the flow on the basis of the angle-dependent attenuation of the intensity, as will be described in more detail below.

By way of example, provision is advantageously made for the output signal of the detector to be suppliable to an evaluation device, in which a variable characterizing the homogeneity of the fluid flow is determined from the angle-dependent intensity captured by the detector.

One particularly preferred embodiment provides that the transmitter emits light in the infrared range, in particular laser light in the near infrared range. In this case, the invention applies the principle of gas analysis on the basis of high-resolution molecular absorption spectrography. In this case, the transmitter can preferably be configured as a diode laser, whereas the detector is formed for example from one or more photodiodes. This embodiment has in particular the great advantage that the influence of cross-sensitivities on the measurement is negligible since the quasi monochromatic laser light in a given scanned spectral range is absorbed very selectively by only one specific molecular line. For this reason, provision is preferably made for the wavelength of the infrared light to be tuned to a specific wavelength of the gas forming the fluid flow and in particular of the gas forming the reducing-agent flow, for example ammonia ($NH_3$).

According to one very advantageous embodiment, the light-transmissive region is formed for example by a concentric, annular ring, which is permeable to infrared light, in particular a sapphire glass ring, and is arranged in the pipe, in particular in the exhaust-gas pipe.

With the concentration of the reducing agent being known, as is determinable in a manner known per se, the intensity which has been captured in an angle-dependent manner is evaluated on the basis of the Beer-Lambert law. A conclusion is reached not only as to the homogeneity, but it is also possible for example to the diameter of the reducing-agent stream, if a reducing-agent thread forms in the pipe, for example, that is to say determine a flow which is delimited with respect to its diameter. The diameter of such a reducing-agent thread can, with a known concentration $c_{red}$, be determined in this case according to the following equation:

$$\frac{I}{I_0} = \exp((-1)S_{\lambda_0}\phi_{\lambda,\lambda_0}c_{red}L),$$

wherein:

I is the intensity of the attenuated transmitted light beam of a wavelength $\lambda$, $I_0$ is the intensity of the non-attenuated light beam of the wavelength $\lambda$, $S_{\lambda,0}$ is the absorption strength $\emptyset_{\lambda,\lambda_0}$ is a correction factor taking into account the deviation of the wavelength, $c_{red}$ is the concentration of the absorbing substance (of the reducing agent), and L is the diameter of the reducing-agent flow.

If the metered-in reducing-agent flow $I_{red}$ is known instead of the concentration $c_{red}$, the diameter can be determined using the following equations:

$$\pi\left(\frac{L}{2}\right)^2 = \frac{I_{red}}{C_{red}} \frac{1}{M_{red}^{mol} v},$$

$$c_{red} = \frac{1}{L}\frac{1}{S_{\lambda_0}\phi_{\lambda,\lambda_0}}\ln\left(\frac{I_{0,light}}{I_{light}}\right).$$

In the equations:

L: is the diameter of the reducing-agent thread, $I_{red}$: is the mass flow rate of the reducing agent, $C_{red}$: is the concentration of the reducing agent, $M^{mol}_{red}$: is the molar mass of the reducing agent, v: is the flow speed, $I_{0,light}$: is the intensity of the non-attenuated light beam of wavelength $\lambda$, $I_{light}$: is the intensity of the attenuated light beam of wavelength $\lambda$, $S_{\lambda,0}$: is the absorption strength, and $\emptyset_{\lambda,\lambda_0}$: is the correction factor owing to deviation of wavelength.

BRIEF DESCRIPTION OF THE DRAWINGS

Exemplary embodiments of the invention are illustrated in the drawings and will be explained in more detail in the following description, in which:

FIG. 1 schematically shows a pipe with a glass ring arranged therein, on the exterior of which pipe the apparatus (not shown) according to the invention for carrying out the method according to the invention can be arranged;

DETAILED DESCRIPTION

Figure 2A:
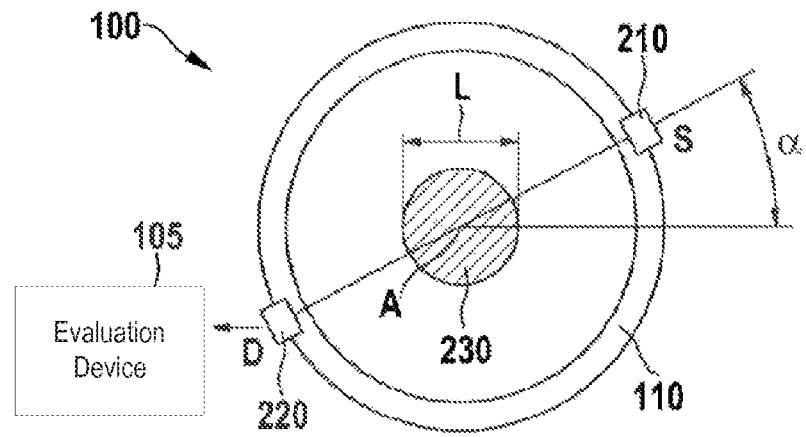
FIG. 2a schematically shows the arrangement of the apparatus according to the invention in the region of the glass ring.

FIG. 1 schematically shows a pipe 100, such as an exhaust-gas pipe, of an internal combustion engine (not shown), which is situated immediately upstream of an SCR catalytic converter (not shown) which is known per se. Provided in this pipe 100 is a transmissive annular region 110, which is formed for example by a sapphire glass ring. In FIG. 1, the right part of the pipe can also already be the SCR catalytic converter itself, with the result that the sapphire glass ring is arranged immediately upstream of the SCR catalytic converter. Arranged on this annular region 110 are—as is illustrated schematically in FIG. 2a—a transmitter 210 and a diametrically opposite detector 220. The transmitter 210 and the detector 220 are coupled and are rotatable together about an axis A, which coincides with the pipe's axis of symmetry. The transmitter 210 is a diode laser, for example, which emits laser light in the near infrared range, which is transmitted through the sapphire glass 110 and received by the detector 220. The wavelength of the laser light is tuned to a specific absorption line of the gas to be measured, that is to say to a specific absorption line for example of the exhaust-gas flow to be measured containing the reducing agent. The arrangement takes advantage, as it were, of the technology of a gas analysis appliance, although an essential feature here is the rotatability of this arrangement through 360°. It should be noted at this point that the present measurement is a measurement of the transmittance of the laser light beam with an angular offset. Rather than, for example, arranging the transmitter 210 and the detector 220 in a rotatable fashion, it is also possible purely as a matter of principle for a plurality of transmitters and diametrically opposite detectors to be arranged on the glass ring 110 and to detect the transmittance simultaneously or successively with chronological offsets. To this end, it is merely necessary to ensure that the light beam emitted by a transmitter only ever strikes the detector that is located opposite the transmitter, that is to say is not incident on another detector owing to scattering. Such an arrangement, however, only allows for a measurement in discrete angular distances, whereas the arrangement of a rotatable transmitter 210 and of a detector 220, which rotates with the transmitter, allows a continuous measurement through the entire angular range of 360° and also requires only a single transmitter 210 and a single detector 220. "Rotatability" and "rotatable" in the present invention therefore not only refer to a continuous rotatability of a transmitter 210 and of a diametrically opposite detector 220, but also to a discrete arrangement of a plurality of transmitters and diametrically opposite detectors in the previous sense, which are in each case offset by specifiable angles. To this extent, it relates to the angularly offset capture of intensity ratios.

Figure 2B:
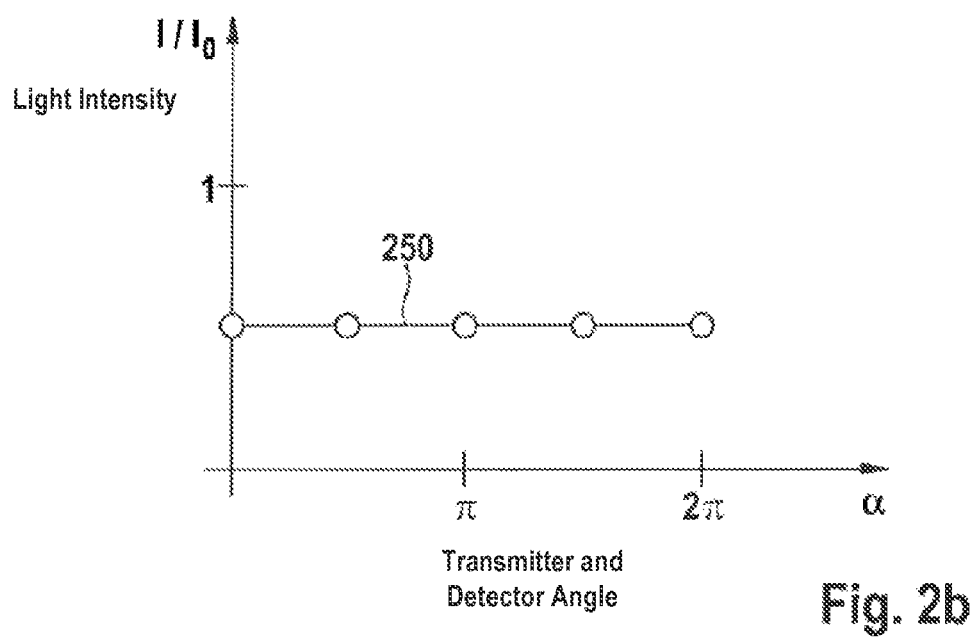
FIG. 2b shows the ratio of the intensity of the transmitted light to the intensity of the incident light over the rotation angle for a reducing-agent thread arranged concentrically around the pipe axis.

By way of example, if a cylindrical reducing-agent thread 230, as schematically illustrated in FIG. 2a, which is arranged concentrically around the pipe axis, that is to say a reducing-agent thread which has a diameter L, which is smaller than the internal diameter of the pipe, flows in the exhaust-gas pipe 100, a rotation of the transmitter 210 and of the detector 220, which is coupled to the transmitter, results in a signal, which is evaluated in an evaluation device 105, over the rotation angle α, for example the ratio of the intensity of the transmitted light I to the intensity of the incident light $I_0$ over the angle α, as is schematically illustrated in FIG. 2b by the line 250. This signal is a constant straight line parallel to the x-axis, wherein $I/I_0 < 1$, because the transmitted light has undergone extinction and thus the intensity I is less than the intensity $I_0$ of the incident light.

Figure 3A:
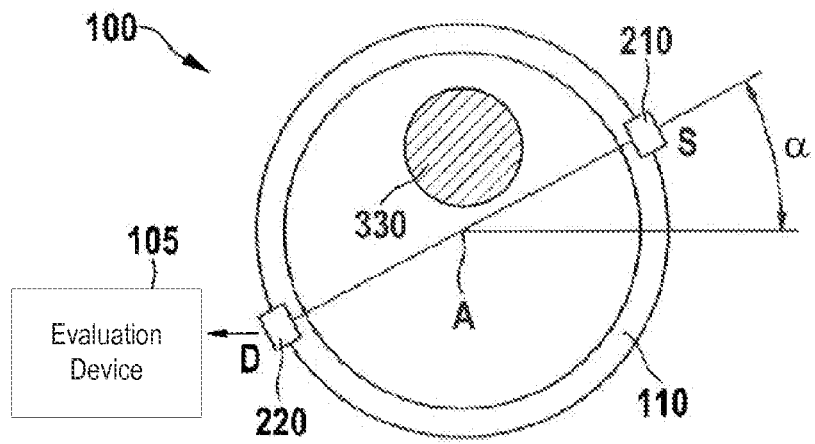
FIG. 3a shows an arrangement corresponding to FIG. 2a for an eccentrically arranged reducing-agent thread.
Figure 3B:
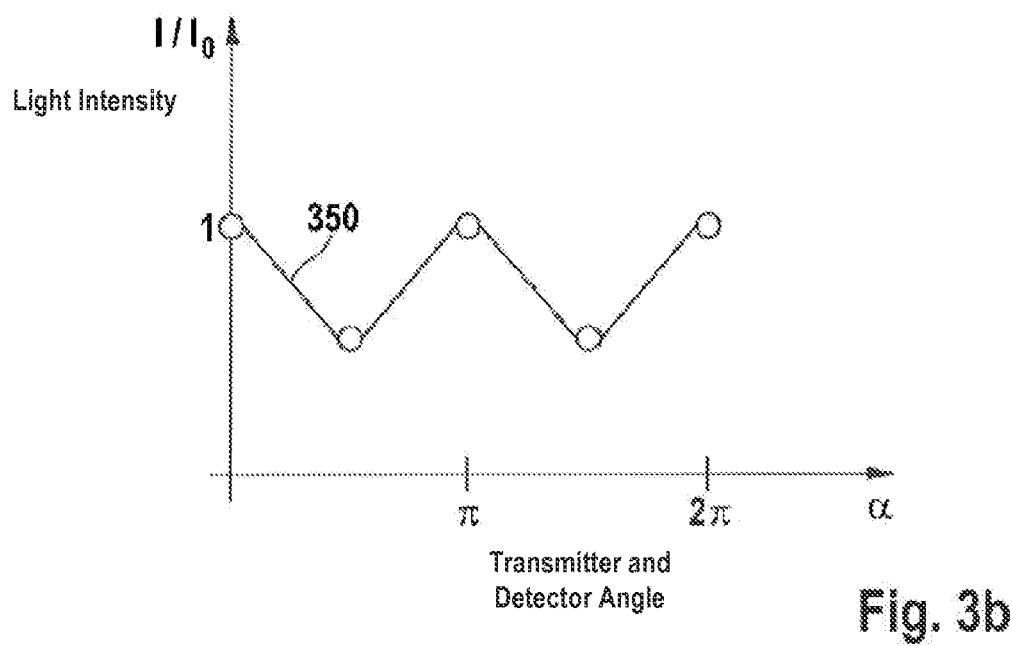
FIG. 3b shows the ratio of the intensity of the transmitted light to the intensity of the incident light for an eccentrically arranged reducing-agent thread.

If, by contrast, such a reducing-agent thread 330 is arranged eccentrically outside of the axis A (pipe axis), as is schematically illustrated for example in FIG. 3a, the result for the signal output by the detector 220 to the evaluation device 105 is a "zigzag" line 350 shown in FIG. 3b. The maxima of this line represent the beam paths, in which the light beam is not transmitted through the reducing-agent thread, that is to say where the light beam does not pass through the reducing-agent thread 330. In this case, the intensity I of the "transmitted" light is equal to the intensity $I_0$ of the incident light and the ratio $I/I_0$ is 1. In-between the maxima are regions, in which partial transmittance of the light beam takes place, up to maximum transmittance whenever the light beam passes through the entire diameter of the reducing-agent thread. These events form the minima of the "zigzag" line 350 in FIG. 3b. On the basis of the ratio of the intensity of the transmitted light I to the intensity of the incident light $I_0$, it is possible to draw conclusions relating to homogeneity as follows:

An eccentrically arranged reducing-agent thread 330 (see FIG. 3a) represents an inhomogeneous reducing-agent flow. A concentrically arranged reducing-agent thread 230 (see FIG. 2a) likewise represents an inhomogeneous reducing-agent flow, since the reducing agent is not distributed over the entire interior of the pipe 100, but is limited to a region of diameter L. A homogeneous reducing-agent flow is defined as a reducing-agent flow which fills the entire interior of the pipe 100, that is to say as a reducing-agent thread with a diameter which corresponds to the internal diameter of the pipe 100. In this case, the ratio of the intensity of the transmitted light I to the intensity of the incident light $I_0$ has a different value than in the case of a reducing-agent thread of diameter L, which is smaller than the internal diameter of the pipe 100. Based on the ratio of the intensity of the transmitted, attenuated light to the intensity of the incident, non-attenuated light, it is thus possible to conclude whether the reducing-agent thread is arranged coaxially to the axis of symmetry A of the pipe, in which case the ratio is constant, or whether it is arranged eccentrically with respect to the axis of symmetry A of the pipe, in which case a "zigzag" line, as described above, is the result. For a reducing-agent thread which is arranged concentrically around the axis of symmetry of the pipe, the ratio of intensities has a different value if the reducing-agent thread has a diameter L, which is smaller than the internal diameter of the pipe, than for a reducing-agent thread which completely fills the inside of the pipe. A reducing-agent thread which completely fills the pipe has a determinable constant value for the ratio of the intensities $I/I_0$. The determination of the ratio $I/I_0$ thus allows a conclusion to be drawn regarding the homogeneity of the fluid flow in the pipe, in particular of the reducing-agent flow in the exhaust-gas pipe of the internal combustion engine, wherein—as already mentioned above—homogeneous fluid flow within the meaning of the present application means that a fluid flow, which completely fills the interior of the pipe, exists in the interior of the pipe.

Purely as a matter of principle it suffices for the angle-dependent dependence of the ratio of the intensity I of the transmitted light to the intensity $I_0$ of the incident light to be determined in order to draw a conclusion as to the homogeneity of the reducing-agent flow on the basis of the dependence of the intensity I on the angle α, that is to say $I(\alpha) = I_0 f(\alpha)$. With a known concentration $c_{red}$ of the reducing-agent flow, it is moreover possible to also calculate the diameter L of the reducing-agent thread. This is done according to one embodiment of the method using the Beer-Lambert law:

$$\frac{I}{I_0} = \exp((-1) S_{\lambda_0} \phi_{\lambda_0} c_{red} L),$$

wherein:
I is the intensity of the attenuated light beam of wavelength λ,
$I_0$ is the intensity of the non-attenuated light beam of wavelength λ,
$S_{\lambda_0}$ is the absorption strength,
$\emptyset_{\lambda,\lambda_0}$ is a correction factor taking into account the deviation of the wavelength,
$c_{red}$ is the concentration of the absorbing substance, and
L is the diameter of the reducing-agent flow.

If, however, the mass flow rate of the reducing agent is known, which can likewise be determined in a manner known per se, it is possible according to another embodiment of the method for the thread diameter L to be determined in the manner described below:

For a given rotation angle α, a minimum intensity is obtained. For this angle, the length of the light path L through the reducing-agent thread is at its maximum. In this case, the following equations apply:

$$\pi \left(\frac{L}{2}\right)^2 = \frac{I_{red}}{C_{red}} \frac{1}{M_{red}^{mol} v}$$

$$c_{red} = \frac{1}{L} \frac{1}{S_{\lambda 0} \phi_{\lambda,\lambda 0}} \ln\left(\frac{I_0}{I}\right).$$

In the equations, the following designations are used:
L: diameter of the reducing-agent thread,
$I_{red}$: mass flow rate of the reducing agent,
$C_{red}$: concentration of the reducing agent,
$M^{mol}_{red}$: molar mass of the reducing agent,
v: flow speed,
$I_0$: intensity of the non-attenuated light beam of wavelength λ,
I: intensity of the attenuated light beam of wavelength λ,
$S_{\lambda 0}$: absorption strength, and
$\emptyset_{\lambda,\lambda 0}$: correction factor owing to deviation of wavelength.

Thus, if the reducing-agent flow, the flow speed, the attenuation of the light beam and the constants are known, it is possible from the two equations to determine both the concentration of the reducing agent $c_{red}$ and the diameter of the reducing-agent thread L.

The invention claimed is:
1. An apparatus configured for determining the homogeneity of a fluid flow passing through the apparatus, the apparatus comprising:
a pipe configured to transport or contain a fluid;
a light-transmissive region of the pipe extending around a circumference of the pipe;
at least one optical transmitter configured to transmit an optical signal through the light-transmissive region of the pipe; and
at least one optical detector positioned diametrically opposite the optical transmitter, the at least one optical detec- tor configured to receive the optical signal from the at least one optical transmitter,
wherein the at least one optical transmitter and the at least one optical detector are each configured in order for the at least one optical detector to detect a variation in intensity of the optical signal that is transmitted through the pipe at a plurality of angles around the circumference of the pipe in order to provide the determination of the homogeneity of the fluid flow from the detected variation of intensity of the optical signal passing through the light-transmissive region that extends around the circumference of the pipe.

2. The apparatus according to claim 1, wherein the at least one optical transmitter and the at least one optical detector are configured in order to rotate around the light transmissive region of the pipe on a rotational axis that is located axial to the pipe.

3. The apparatus according to claim 1,
wherein the at least one optical transmitter includes a plurality of optical transmitters, and
wherein the at least one optical detector includes a plurality of optical detectors, each one of the plurality of optical detectors being configured to receive an optical signal from a respective one of the plurality of optical transmitters,
wherein the plurality of optical transmitters and the plurality of optical detectors are arranged at intervals around the circumference e of the pipe such that each pairing of one of the plurality of optical transmitters and a corresponding one of the plurality of optical detectors is positionally offset with respect to each other by specifiable angles.

4. The apparatus according to claim 1, wherein a signal indicative of the amplitude of the optical signal received by the at least one optical detector is transmitted to an evaluation device, in which a variable characterizing the homogeneity of the fluid flow is then determined from an angle-dependent intensity of same optical signal which was received by the at least one optical detector.

5. The apparatus according to claim 1, wherein the at least one optical transmitter emits light in the infrared range as the optical signal.

6. The apparatus according to claim 5, wherein the wavelength of the infrared light is tuned to a specific wavelength based on a gas forming the fluid flow through the pipe.

7. The apparatus according to claim 1, wherein the light-transmissive region is formed by a concentric, annular ring, which is permeable to infrared light passing through the concentric, annular ring.

8. A method of determining a homogeneity of a fluid flow in a pipe, the method comprising:
transmitting, with at least one optical transmitter, an optical signal from said at least one optical transmitter through a light-transmissive region of the pipe, the light-transmissive region extending around a complete circumference of the pipe;
detecting with at least one optical detector that is positioned diametrically opposite the at least one optical transmitter, an intensity of the optical signal that is indicative of the light absorption of the fluid flow in the pipe; and
determining the homogeneity of the fluid flow in the pipe, based on the intensity of the detected optical signal at a plurality of angles around the complete circumference of the pipe; and
providing the determined homogeneity of the fluid flow in the pipe as a viewable output on a display device.

9. The method according to claim 8, wherein the at least one optical transmitter and the at least one optical detector are rotated through the range of 360° about the rotational axis which is located substantially along the longitudinal axis of the pipe.

10. The method according to claim 8, wherein a plurality of optical transmitters and a plurality of optical detectors are arranged offset from one another, in each case by specifiable angles, and
wherein the plurality of optical transmitters and the plurality of optical detectors simultaneously or successively capture the intensity of the optical signal over the plurality of angles extending around the complete circumference of the pipe.

11. The method according to claim 8, wherein the fluid flow through the pipe causes attenuation of the optical signal, and further comprises the steps of:
determining a level of optical signal attenuation corresponding to the rotation angle;
determining the homogeneity of a reducing-agent flowing in the pipe on the basis of the optical signal attenuation and the angle dependence of the optical signal attenuation;
wherein the optical signal attenuation is based on the intensity of the transmitted optical signal and the intensity of the detected optical signal.

12. The method according to claim 11, wherein determining the homogeneity of the fluid flow includes determining when a ratio of the intensity of the transmitted, attenuated optical signal to the intensity of a detected, non-attenuated optical signal over a rotation angle of 360° assumes a specific specifiable constant path.

13. The method according to claim 8, wherein, on the basis of the intensity of the detected optical signal, which is captured in an angle-dependent manner, a diameter of the reducing-agent flowing in the pipe is determined based on the Beer-Lambert law of determining a known concentration of the reducing agent according to the following equation $$\frac{I}{I_0} = \exp((-1)S_{\lambda_0}\phi_{\lambda_0}c_{red}L),$$

wherein:
I is the intensity of the attenuated light beam of a wavelength $\lambda$,
$I_0$ is the intensity of the non-attenuated light beam of the wavelength $\lambda$,
$S_{\lambda_0}$ is the absorption strength,
$\emptyset_{\lambda,\lambda_0}$ is a correction factor taking into account the deviation of the wavelength,
$c_{red}$ is the concentration of the reducing agent, and
L is the diameter of the reducing-agent flow.

14. The method according to claim 8, wherein, on the basis of the intensity, which is captured in an angle-dependent manner, the concentration of the reducing agent and the diameter of the reducing-agent flowing in the pipe are determined with respect to a known metered-in reducing-agent mass flow rate according to the following equations:

$$\pi\left(\frac{L}{2}\right)^2 = \frac{I_{red}}{C_{red}}\frac{1}{M_{red}^{mol}v}$$

-continued
$$c_{red} = \frac{1}{L} \frac{1}{S_{\lambda 0} \phi_{\lambda,\lambda 0}} \ln\left(\frac{I_0}{I}\right),$$

wherein:
L: diameter of the reducing-agent thread,
$I_{red}$: mass flow rate of the reducing agent,
$C_{red}$: concentration of the reducing agent,
$M^{mol}_{red}$: molar mass of the reducing agent,
v: flow speed,
$I_0$: intensity of the non-attenuated light beam of wavelength A,
I: intensity of the attenuated light beam of wavelength A,
$S_{\lambda 0}$: absorption strength, and
$\emptyset_{\lambda,\lambda 0}$: correction factor owing to deviation of wavelength.

* * * * *